US005929163A

United States Patent [19]

Harashima

[11] Patent Number: 5,929,163
[45] Date of Patent: Jul. 27, 1999

[54] SILICONE GEL COMPOSITION

[75] Inventor: Asao Harashima, Tokyo, Japan

[73] Assignee: Dow Corning Toray Silicone Co., LTD., Tokyo, Japan

[21] Appl. No.: 08/054,998

[22] Filed: Apr. 29, 1993

[30] Foreign Application Priority Data

May 1, 1992 [JP] Japan ........ 4-140043

[51] Int. Cl.[6] ........ C08G 77/04
[52] U.S. Cl. ........ 524/837; 424/70.12
[58] Field of Search ........ 524/837; 424/70.12

[56] References Cited

U.S. PATENT DOCUMENTS

| | | | |
|---|---|---|---|
| 4,311,695 | 1/1982 | Starch | 424/184 |
| 4,421,769 | 12/1983 | Dixon et al. | 424/358 |
| 4,814,376 | 3/1989 | Tanaka et al. | 524/837 |

FOREIGN PATENT DOCUMENTS

| | | |
|---|---|---|
| 61-212324 | 9/1986 | Japan . |
| 62-045656 | 2/1987 | Japan . |
| 62-054759 | 3/1987 | Japan . |

OTHER PUBLICATIONS

61113646 Japanese Laid open (abstract).
61066752 abstract.

*Primary Examiner*—Robert Dawson
*Attorney, Agent, or Firm*—James L. De Cesare

[57] ABSTRACT

A silicone gel composition that contains (a) a silicone oil, (b) a polyoxyalkylene group-containing organopolysiloxane with the formula

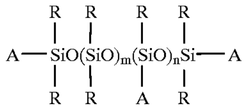

wherein R is the methyl or phenyl group; A is the methyl group, phenyl group, or polyoxyalkylene groups with the formula $$-C_3H_6O(C_2H_4O)_a(C_3H_6O)_bR'$$

wherein R' is the hydrogen atom, an acyl group, or alkyl groups having 1 to 4 carbon atoms, a is an integer with a value of 5 to 50, and b is an integer with a value of 5 to 50;

m is an integer with a value of 50 to 1,000; and n is an integer with a value of 1 to 40, and (c) water.

1 Claim, No Drawings

SILICONE GEL COMPOSITION

BACKGROUND OF THE INVENTION

The present invention relates to a silicone gel composition and, more specifically, relates to a silicone gel composition that gives a light, dry sensation or feel and that is very stable with respect to time.

Silicone oils are nontoxic, highly spreadable, highly lubricating, and very water repellent, and for these reasons are employed in such products as cosmetics, makeup, skin-care cosmetics, hair-care cosmetics, and pharmaceutical products. Silicone oils have been available in the form of water-based silicone emulsion compositions, silicone oil compositions, and silicone gel compositions. Silicone gel compositions have been used for sunscreen gels, moisturizing creams, antiperspirant creams, liquid foundations, and hair gels. Known silicone gel compositions include silicone gel compositions composed of silicone oil and wax and silicone gel compositions composed of silicone oil and silica or lipophilic silica. However, it is difficult to smoothly spread the wax-containing silicone gel compositions on the skin or hair, and once applied these compositions give a clammy feel. On the other hand, the silica-containing silicone gel compositions have poor keeping qualities because the silica aggregates and the silicone oil separates out. In response to this, Japanese Patent Application Laid Open [Kokai or Unexamined] Number Sho 61-113646 [113,646/1986] has proposed a silicone gel composition that consists of silicone oil, a polyoxyalkylene-containing organopolysiloxane, an organically modified clay mineral such as dioctadecyldimethylammonium salt-modified montmorillonite and water.

Nevertheless, the organically modified clay mineral still aggregates and the silicone oil still separates out with elapsed time in the case of the silicone gel composition proposed in Japanese Patent Application Laid Open Number Sho 61-113646. Furthermore, this silicone gel composition still provides a clammy feel when applied to the skin or hair.

SUMMARY OF THE INVENTION

The present invention takes as its object the introduction of a silicone gel composition that gives a light, dry sensation and that is very stable with respect to time.

DETAILED DESCRIPTION OF THE INVENTION

The present invention relates to a silicone gel composition that consists of (a) a silicone oil, (b) a polyoxyalkylene group-containing organopolysiloxane with the formula

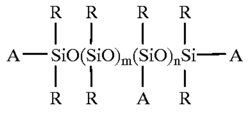

wherein R is the methyl or phenyl group; A is selected from the group consisting of the methyl group, phenyl group, and polyoxyalkylene groups with the formula $$-C_3H_6O(C_2H_4O)_a(C_3H_6O)_bR'$$

wherein R' is selected from the group consisting of the hydrogen atom, an acyl group, and alkyl groups having 1 to 4 carbon atoms, a is an integer with a value of 5 to 50, and b is an integer with a value of 5 to 50;

m is an integer with a value of 50 to 1,000; and n is an integer with a value of 1 to 40, and (c) water.

The silicone oil comprising component (a) is exemplified by low- to high-viscosity diorganopolysiloxanes such as dimethylpolysiloxanes, methylphenylpolysiloxanes, and dimethylsiloxane-methylphenylsiloxane copolymers; cyclic siloxanes such as octamethylcyclotetrasiloxane, decamethylcyclopentasiloxane, and tetramethyltetraphenyltetracyclosiloxane; cyclic siloxane solutions of high degree-of-polymerization dimethylpolysiloxane gums, dimethylsiloxane-methylphenylsiloxane copolymer gums, and dimethylpolysiloxane gums; trimethylsiloxysilicic acids and the cyclic siloxane solutions of trimethylsiloxysilicic acids; diorganopolysiloxanes having $C_{6-50}$ alkyl groups; and amino-containing diorganopolysiloxanes. Component (a) can take the form of a single species of silicone oil as exemplified above or a mixture of two or more such silicone oils.

The content of component (a) in the silicone gel composition of the present invention is not specifically restricted, but the preferred range for the component (a) content is 20 to 95 weight %.

Component (b) functions as gelling agent in the present invention. Component (b) is a polyoxyalkylene group-containing organopolysiloxane with the following general formula:

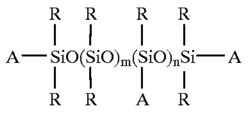

The group R in this formula is the methyl or phenyl group, while A is the methyl group, phenyl group, or a polyoxyalkylene group with the following general formula:

$$-C_3H_6O(C_2H_4O)_a(C_3H_6O)_bR'$$

The group R' in this polyoxyalkylene group is the hydrogen atom, an acyl group, or an alkyl group having 1 to 4 carbon atoms. Acyl groups are exemplified by formyl, acetyl, propionyl, butyryl, acryloyl, benzoyl, and toluoyl. The $C_{1-4}$ alkyl groups are specifically exemplified by methyl, ethyl, isopropyl, n-propyl, tert-butyl, and n-butyl. Moreover, a is an integer with a value of 5 to 50 and b is also an integer with a value of 5 to 50. The ranges for the polyoxyalkylene group in component (b) are such that when a or b is below 5, component (b) is no longer able to provide a satisfactory thickening activity; and when a or b exceeds 50, the resulting silicone gel composition gives a clammy sensation. The polyoxyalkylene group content in component (b) is not specifically restricted, but the preferred polyoxyalkylene group content falls within the range of 20 to 70 weight % exclusive of 20 weight %. Component (b) has a sharply reduced thickening activity when the polyoxyalkylene group content in component (b) is ≦20 weight %. On the other hand, a content in excess of 70 weight % results in a loss of compatibility with component (a).

In addition, m is an integer with a value of 50 to 1,000 and n is an integer with a value of 1 to 40. The thickening activity is unsatisfactory when m falls below 50 and n falls below 1. On the other hand, the resulting silicone gel composition gives a clammy sensation when m exceeds 1,000 and n exceeds 40.

The organopolysiloxane comprising component (b) is exemplified by the following organopolysiloxanes:

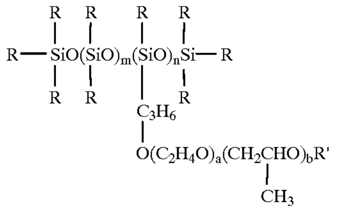

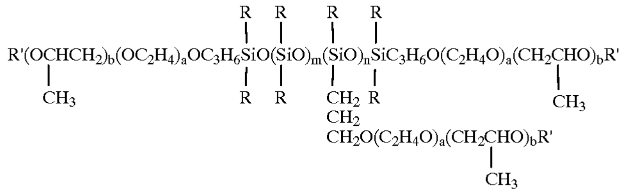

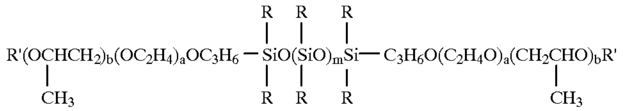

Neither the molecular weight of component (b) nor its viscosity at 25° C. are specifically restricted. However, preferred viscosities for the 50 weight % octamethylcyclotetrasiloxane solution of component (b) fall within the range of 1,000 to 100,000 centistokes because this leads to the formation of a stable gel that gives a light, dry sensation.

The component (b) content is also not specifically restricted in the present invention, but its preferred range is 2 to 30 weight % and its particularly preferred range is 5 to 15 weight %. A stable silicone gel composition cannot be obtained when the silicone gel composition of the present invention contains less than 2 weight % component (b). When the component (b) content exceeds 30 weight %, the silicone gel composition will give a clammy feeling.

The silicone gel composition of the present invention is prepared by mixing water into the components (a) and (b). The content of water in the silicone gel composition of the present invention preferably falls within the range of 0.2 to 80 weight % and particularly preferably falls within the range of 0.3 to 75 weight %. A stable silicone gel composition cannot be prepared when the water content falls below 0.2 weight %. When the water content exceeds 80 weight %, the water will separate from the silicone gel composition, and the preparation of a stable silicone gel composition becomes difficult.

The silicone gel composition of the present invention is storage stable, and it affords a light, dry sensation when applied to the skin or hair. These qualities make it ideal for application in cosmetics. For its cosmetic applications, the silicone gel composition of the present invention may be blended as desired with such cosmetic additives as waxes, oils and fats, lower alcohols, lower polyhydric alcohols, higher alcohols, esters, moisture-retention agents, pigments, antiperspirants, UV absorbers, fragrances, and preservatives.

Furthermore, due to its excellent keeping qualities and light, dry feel, the silicone gel composition of the present invention can be used in pharmaceutical products, automotive polishes, and furniture polishes.

The present invention is explained in greater detail below through illustrative examples, but the present invention is not limited thereby. Table 1 shows the organopolysiloxanes used as component (b) in the examples. The structures of the organopolysiloxane referenced in Table 1 are shown below.

Type I

Type I

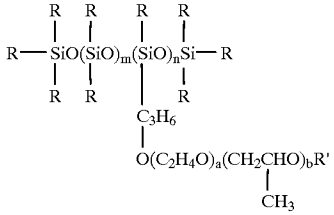

Type II

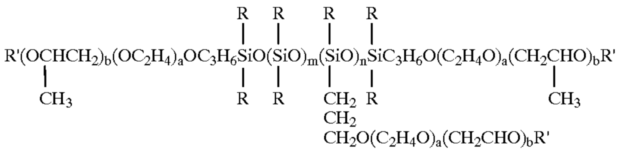

-continued

Type III

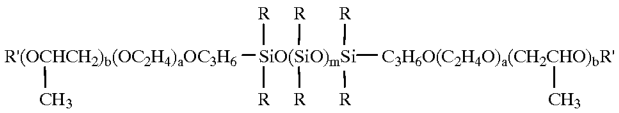

TABLE 1

| organopoly-siloxane | type | R | m | n | a | b | $R^1$ |
|---|---|---|---|---|---|---|---|
| A | I | methyl | 400 | 4 | 20 | 20 | H |
| B | I | methyl | 400 | 7 | 20 | 20 | H |
| C | I | methyl | 400 | 10 | 20 | 20 | H |
| D | I | methyl | 400 | 12 | 20 | 20 | H |
| E | I | methyl | 400 | 15 | 20 | 20 | H |
| F | I | methyl | 400 | 15 | 20 | 20 | $CH_3$ |
| G | I | methyl | 400 | 20 | 20 | 20 | H |
| H | I | methyl | 250 | 3 | 25 | 25 | H |
| I | I | methyl | 250 | 3 | 25 | 0 | H |
| J | I | methyl | 70 | 3 | 8 | 5 | H |
| K | I | methyl | 70 | 3 | 13 | 0 | H |
| L | II | methyl | 400 | 8 | 25 | 25 | H |
| M | II | methyl | 400 | 8 | 25 | 4 | H |
| O | III | methyl | 300 | — | 30 | 15 | H |
| P | III | methyl | 300 | — | 30 | 0 | H |
| Q | III | methyl/phenyl = 80/20 | 500 | — | 40 | 60 | $C_4H_9$ |
| R | III | methyl/phenyl = 80/20 | 500 | — | 3 | 60 | $C_4H_9$ |

The stability with respect to time was measured as follows.

Appearance

The silicone composition was sampled into a 100 cc sample bottle, and the appearance was visually inspected after standing for 30 days at room temperature.

Viscosity

Using a VDA rotary viscometer, the viscosity of the silicone gel composition was measured both immediately after preparation and again after standing for 30 days at room temperature.

Application sensation

The spreadability and sensation were evaluated when the silicone composition was applied to the skin.

EXAMPLE 1

10 weight parts of the organopolysiloxane was dispersed into 90 weight parts of the silicone oil by stirring. Into this was mixed 1 weight part of the ultraviolet absorber Escalol 507 from Van Dyk Company, Inc. followed by the dropwise addition of 2 weight parts water while mixing. A sunscreen gel was subsequently obtained by dispersion to homogeneity in a homomixer. These sunscreen gels were very spreadable and gave a light, dry feeling. Tables 2, 3, 4, and 5 show the appearance and viscosity for each product both immediately after preparation and after standing for 30 days at room temperature.

TABLE 2

| | Example 1 | Example 2 | Example 3 | Example 4 |
|---|---|---|---|---|
| silicone oil | | | | |
| decamethylpenacyclosiloxane | | | + | + |
| 2 wt % decamethylpentacyclosiloxane solution of silicone gum | + | | | |
| dimethylpolysiloxane (10 cs) | | + | | |
| organopolysiloxane | | | | |
| A | + | | | |
| B | | + | | |
| C | | | + | |
| D | | | | + |
| appearance | | | | |
| immediately after preparation | transparent | transparent | transparent | transparent |
| after 30 days | transparent | transparent | transparent | transparent |
| stability | | | | |
| immediately after preparation | no separation | no separation | no separation | no separation |
| after 30 days | no separation | no separation | no separation | no separation |
| viscosity (cps) rotor no. 3, 0.6 rpm | | | | |
| immediately after preparation | 116,000 | 138,000 | 109,800 | coule not be measured |
| after 30 days | 112,000 | 142,000 | 110,000 | could not be measured |
| viscosity (cps) rotor no. 4, 3 rpm | | | | |
| immediately after preparation | 48,000 | 78,900 | 43,800 | could not be measured |
| after 30 days | 49,000 | 75,600 | 41,000 | could not be measured |

TABLE 3

| | Example 5 | Example 6 | Example 7 | Example 8 |
|---|---|---|---|---|
| silicone oil | | | | |
| decamethylpentacyclosiloxane | + | + | + | + |
| organopolysiloxane | | | | |
| E | + | | | |
| F | | + | | |
| G | | | + | |
| H | | | | + |
| appearance | | | | |
| immediately after preparation | transparent | transparent | transparent | transparent |
| after 30 days | transparent | transparent | transparent | transparent |
| stability | | | | |
| immediately after preparation | no separation | no separation | no separation | no separation |
| after 30 days | no separation | no separation | no separation | no separation |
| viscosity (cps)<br>rotor no. 3, 0.6 rpm | | | | |
| immediately after preparation | 95,600 | 77,000 | 11,600<br>rotor no. 2<br>0.6 rpm | 17,200<br>rotor no. 2<br>1.5 rpm |
| after 30 days | 89,000 | 76,000 | 11,400<br>rotor no. 2<br>0.6 rpm | 13,300<br>rotor no. 2<br>1.5 rpm |
| viscosity (cps)<br>rotor no. 4, 3 rpm | | | | |
| immediately after preparation | 39,400 | 35,000 | 3,800<br>rotor no. 2<br>3 rpm | 5,200<br>rotor no. 3<br>6 rpm |
| after 30 days | 39,000 | 32,000 | 3,850<br>rotor no. 2<br>3 rpm | 4,900<br>rotor no. 3<br>6 rpm |

TABLE 4

| | Comp. Ex. 1 | Example 9 | Comp. Ex. 2 | Example 10 | Comp. Ex. 3 |
|---|---|---|---|---|---|
| silicone oil | | | | | |
| decamethylpentacyclosiloxane | + | + | + | + | + |
| organopolysiloxane | | | | | |
| I | + | | | | |
| J | | + | | | |
| K | | | + | | |
| L | | | | + | |
| M | | | | | + |
| appearance | | | | | |
| immediately after preparation | cloudy white | transparent | cloudy white | transparent | transparent |
| after 30 days | precipitate<br>present | transparent | precipitate<br>present | transparent | precipitate<br>present |
| stability | | | | | |
| immediately after preparation | no separation | no separation | no separation | no separation | no separation |
| after 30 days | separated<br>into 2 phases | no separation | separated<br>into 2 phases | no separation | separated<br>into 2 phases |
| viscosity (cps)<br>rotor no. 2, 1.5 rpm | | | | | |
| immediately after preparation | 580<br>rotor no. 1<br>1.5 rpm | 5,600 | 110<br>rotor no. 1<br>1.5 rpm | 16,000 | 15,000 |
| after 30 days | 66<br>rotor no. 1<br>30 rpm | 6,300 | 60<br>rotor no. 1<br>30 rpm | 13,000 | 6,000 |
| viscosity (cps) | | | | | |

TABLE 4-continued

| | Comp. Ex. 1 | Example 9 | Comp. Ex. 2 | Example 10 | Comp. Ex. 3 |
|---|---|---|---|---|---|
| rotor no. 3, 6 rpm | | | | | |
| immediately after preparation | 560<br>rotor no. 1<br>6 rpm | 2,300 | 120<br>rotor no. 1<br>6 rpm | 2,750 | 5,250 |
| after 30 days | 57<br>rotor no. 1<br>30 rpm | 2,150 | 45<br>rotor no. 1<br>30 rpm | 2,700 | 1,000 |

TABLE 5

| | Example 11 | Comparison Example 4 | Example 12 | Comparison Example 5 |
|---|---|---|---|---|
| silicone oil | | | | |
| 20 wt % decamethyltetracyclosiloxane solution of dimethylsiloxane/methyl-phenylsiloxane copolymer | + | + | + | + |
| polyether-modified silicone | | | | |
| O | + | | | |
| P | | + | | |
| Q | | | + | |
| R | | | | + |
| appearance | | | | |
| immediately after preparation | transparent | cloudy white | transparent | transparent |
| after 30 days | transparent | precipitate present | transparent | transparent |
| stability | | | | |
| immediately after preparation | no separation | no separation | no separation | no separation |
| after 30 days | no separation | separated into 2 phases | no separation | no separation |
| viscosity (cps) rotor no. 1, 1.5 rpm | | | | |
| immediately after preparation | 19,000 | 470<br>rotor no. 1<br>1.5 rpm | 5,600 | 2,000 |
| after 30 days | 18,500 | 58<br>rotor no. 1<br>30 rpm | 6,300 | 1,100<br>rotor no. 1<br>1.5 rpm |
| viscosity (cps) rotor no. 3, 6 rpm | | | | |
| immediately after preparation | 5,750 | 493<br>rotor no. 1<br>6 rpm | 2,300 | 1,350<br>rotor no. 2<br>6 rpm |
| after 30 days | 5,500 | 57<br>rotor no. 1<br>30 rpm | 2,150 | 250<br>rotor no. 1<br>6 rpm |

EXAMPLE 2

2 weight parts of the organopolysiloxane were dispersed in 18 weight parts of the silicone oil by stirring (solution A). Separately, 1 weight part sodium chloride and 4 weight parts glycerol were dissolved with stirring in 75 weight parts water (solution B). Solution B was gradually dripped into the stirred solution A, and, after the completion of this addition, a moisturizing cream was obtained by stirring in a homomixer for 5 minutes at 3,000 rpm. The obtained moisturizing creams were very spreadable and gave a light, dry feel. For each product Table 6 shows the results for the appearance and viscosity both immediately after preparation and after standing for 30 days at room temperature.

TABLE 6

| | Example 13 | Example 14 | Comparison Example 6 |
|---|---|---|---|
| silicone oil | | | |
| 1 wt % decamethyl-tetracyclosiloxane solution of silicone gum | + | + | + |
| organopolysiloxane | | | |
| B | + | | |
| D | | + | |

TABLE 6-continued

| | Example 13 | Example 14 | Comparison Example 6 |
|---|---|---|---|
| I | | | + |
| appearance | | | |
| immediately after preparation | uniformly cloudy white | uniformly cloudy white | uniformly cloudy white |
| after 30 days | uniformly cloudy white | uniformly cloudy white | nonuniform, cloudy white |
| stability | | | |
| immediately after preparation | no separation | no separation | no separation |
| after 30 days | no separation | no separation | separated into 3 phases |
| viscosity (cps) rotor no. 2, 1.5 rpm | | | |
| immediately after preparation | 9,600 | 16,500 | 4,800 |
| after 30 days | 9,700 | 17,000 | 1,100 |

EXAMPLE 3

4 weight parts of the organopolysiloxane were dispersed in 60 weight parts of the silicone oil by stirring. 36 weight parts 50% aqueous aluminum chlorohydrate solution ACH303 from Dow Corning Corporation was gradually dripped in while dispersing. After completion of addition, an antiperspirant cream was obtained by mixing for 5 minutes at 3,000 rpm in a homomixer. The resulting antiperspirant creams had a good spreadability and gave a light, dry feel. For each product Table 7 shows the appearance both immediately after preparation and after standing for 30 days at room temperature.

TABLE 7

| | Example 15 | Comparison Example 7 |
|---|---|---|
| silicone oil | | |
| 1 wt % decamethylpentacyclosiloxane solution of silicone gum | + | + |
| organopolysiloxane | | |
| L | + | |
| M | | + |
| appearance | | |
| immediately after preparation | uniform, microturbid | uniformly cloudy white |
| after 30 days | uniform, microturbid | nonuniform, cloudy white |
| stability | | |
| immediately after preparation | no separation | no separation |
| after 30 days | no separation | separation of water |
| condition | | |
| immediately after preparation | cream | cream |
| after 30 days | cream | separation |

EXAMPLE 4

10 weight parts of the organopolysiloxane were stirred into 60 weight parts of the silicone oil followed by the gradual addition with mixing of 20 weight parts pigment comprising a 5:19:20:0.5 ratio mixture of silicone-treated titanium oxide:silicone-treated sericite:silicone-treated talc:and silicone-treated iron oxide red. Additional mixing and dispersion was then carried out in a ball mill for 3 hours. A liquid foundation was prepared by dripping 10 weight parts 50 weight % aqueous 1,4-butanediol solution into 90 weight parts of the fluid mixed pigment dispersion while mixing. The resulting foundations had a good spreadability and gave a light, dry feel. Table 8 shows the properties evaluated for each product both immediately after preparation and after standing for 1 month at room temperature.

TABLE 8

| | Example 16 | Example 17 | Comparison Example 8 |
|---|---|---|---|
| silicone oil | | | |
| 80:6:14 liquid mixture of dimethylpolysiloxane (10 cs):silicone gum:trimethylsiloxysilicic acid | + | + | + |
| organopolysiloxane | | | |
| C | + | | |
| D | | + | |
| K | | | + |
| appearance | | | |
| immediately after preparation | uniform flesh color | uniform flesh color | uniform flesh color |
| after 30 days | uniform flesh color | uniform flesh color | pigment sedimentation |
| stability | | | |
| immediately after preparation | no separation | no separation | no separation |
| after 30 days | no separation | no separation | color phase separation |
| condition | | | |
| immediately after preparation | cream | cream | cream |
| after 30 days | cream | cream | solidification of lower layer |

EXAMPLE 5

50 weight parts of the silicone oil and 30 weight parts isoparaffin which was Isosol 300 from Nippon Sekiyu Kabushiki Kaisha were mixed, and 10 weight parts of the organopolysiloxane was then dispersed into the mixture. Dispersion/mixing of 10 weight parts 50 weight % aqueous propylene glycol solution gave a hair gel composition. When applied to the hair, the hair gel compositions were very spreadable and gave a light, dry feel. Table 9 shows the properties evaluated for each product both immediately after preparation and after standing for 1 month at room temperature.

TABLE 9

| | Example 18 | Comparison Example 9 |
|---|---|---|
| silicone oil | | |
| 1 wt % decamethyltetracyclosiloxane solution of silicone gum | + | + |

TABLE 9-continued

| | Example 18 | Comparison Example 9 |
|---|---|---|
| organopolysiloxane | | |
| D | + | |
| K | | + |
| appearance | | |
| immediately after preparation | uniform, microturbid | uniformly cloudy white |
| after 30 days | uniform, microturbid | nonuniform, cloudy white |
| stability | | |
| immediately after preparation | no separation | no separation |
| after 30 days | no separation | separation of water |
| condition | | |
| immediately after preparation | gel | cream |
| after 30 days | gel | separation |

The silicone gel composition of the present invention is characterized by its excellent storage stability and by its ability to provide a light, dry feel when applied to the skin or hair.

Other variations and modifications may be made in the compounds, compositions, and methods described herein without departing from the essential features and concepts of the present invention. The forms of the invention described herein are exemplary only and are not intended as limitations on the scope of the invention as defined in the appended claims.

That which is claimed is:

1. A silicone gel comprising (a) 20–95 percent by weight of a silicone oil selected from the group consisting of dimethylpolysiloxanes, methylphenylpolysiloxanes, dimethylsiloxane-methylphenylsiloxane copolymers; octamethylcyclotetrasiloxane, decamethylcyclopentasiloxane, tetramethyltetraphenyltetracyclosiloxane; cyclic siloxane solutions of dimethylpolysiloxane gums, dimethylsiloxane-methylphenylsiloxane copolymer gums, and dimethylpolysiloxane gums; trimethylsiloxysilicic acids and cyclic siloxane solutions of trimethylsiloxysilicic acids; diorganopolysiloxanes having $C_{6-50}$ alkyl groups; and amino-containing diorganopolysiloxanes;

(b) 2–30 percent by weight of a polyoxyalkylene organopolysiloxane with a formula selected from the group consisting of

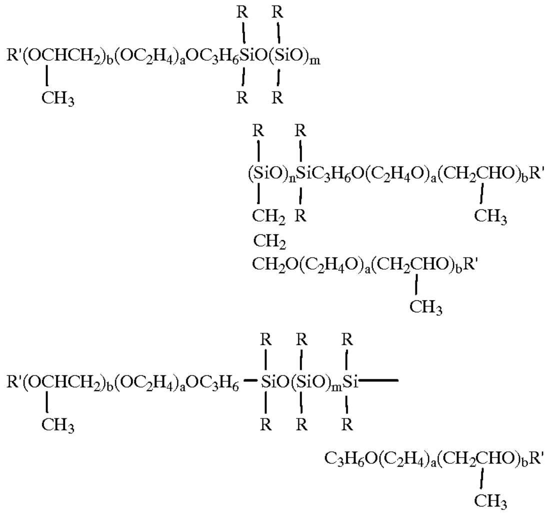

wherein R is the methyl or phenyl group;

R' is selected from the group consisting of the hydrogen atom, an acyl group, and alkyl groups having 1 to 4 carbon atoms, a is an integer with a value of 5 to 50, b is an integer with a value of 5 to 50;

m is an integer with a value of 50 to 1,000; and n is an integer with a value of 1 to 40;

and (c) 0.2–80 percent by weight of water.

* * * * *